US012599761B2

(12) United States Patent　　　(10) Patent No.:　US 12,599,761 B2

Wasserman et al.　　　(45) Date of Patent:　　Apr. 14, 2026

(54) SYSTEMS AND METHODS FOR REMOVING AND REPLACING CONDUCTIVE ADHESIVE LAYERS OF AN ELECTRODE ARRAY

(71) Applicant: NOVOCURE GMBH, Root (CH)

(72) Inventors: Yoram Wasserman, Haifa (IL); Stas Obuchovsky, Haifa (IL); Nataliya Kuplennik, Haifa (IL); David Shapiro, Haifa (IL)

(73) Assignee: NOVOCURE GMBH, Baar (CH)

( * ) Notice: Subject to any disclaimer, the term of this patent is extended or adjusted under 35 U.S.C. 154(b) by 498 days.

(21) Appl. No.: 18/067,373

(22) Filed: Dec. 16, 2022

(65) Prior Publication Data

US 2023/0191116 A1　　Jun. 22, 2023

Related U.S. Application Data

(60) Provisional application No. 63/291,013, filed on Dec. 17, 2021.

(51) Int. Cl.
　　*A61N 1/04*　　　(2006.01)
　　*A61N 1/36*　　　(2006.01)
　　*A61N 1/40*　　　(2006.01)
(52) U.S. Cl.
　　CPC ............... *A61N 1/0496* (2013.01); *A61N 1/40* (2013.01)
(58) Field of Classification Search
　　CPC ...... A61N 1/0496; A61N 1/40; A61N 1/0492; A61N 1/36014
　　See application file for complete search history.

(56) References Cited

U.S. PATENT DOCUMENTS

| | | | | |
|---|---|---|---|---|
| 6,038,464 A | * | 3/2000 | Axelgaard | A61B 5/259 |
| | | | | 600/397 |
| 6,731,987 B1 | * | 5/2004 | McAdams | A61N 1/0436 |
| | | | | 607/152 |
| 2008/0221631 A1 | * | 9/2008 | Dupelle | A61N 1/0492 |
| | | | | 607/5 |
| 2018/0117302 A1 | * | 5/2018 | Clegg | A61B 5/6833 |
| 2021/0346693 A1 | | 11/2021 | Deslauriers | |
| 2022/0218983 A1 | * | 7/2022 | Brooks | A61B 18/1206 |
| 2023/0065587 A1 | * | 3/2023 | Shnaiderman | A61B 5/268 |

FOREIGN PATENT DOCUMENTS

WO　　WO 2019/119045　　6/2019

OTHER PUBLICATIONS

Search Report and Written Opinion of corresponding PCT Application No. PCT/IB2022/062396, dated Mar. 15, 2023.

* cited by examiner

*Primary Examiner* — Joseph A Stoklosa
*Assistant Examiner* — Annie L Shoulders
(74) *Attorney, Agent, or Firm* — Ballard Spahr LLP

(57)　　　　ABSTRACT

An apparatus can include a subassembly having one or more electrode elements, each electrode element having a skin-facing side and a skin-facing surface. The apparatus can further comprise a skin contact layer comprising a conductive adhesive. The skin contact layer can be coupled to the subassembly and can be disposed on the skin-facing side of the electrode elements. The conductive adhesive is electrically coupled to the electrode and configured to contact skin of a subject. At least a portion of the skin contact layer is selectively removable from the subassembly.

20 Claims, 6 Drawing Sheets

X1    X2    X3

X4    X5    X6

X7    X8    X9

40

40

X7    X8    X9

CERAMIC     CERAMIC     CERAMIC
HYDROGEL    HYDROGEL    HYDROGEL

SKIN

SYSTEMS AND METHODS FOR REMOVING AND REPLACING CONDUCTIVE ADHESIVE LAYERS OF AN ELECTRODE ARRAY

CROSS-REFERENCE TO RELATED APPLICATION

This application claims priority to, and the benefit of the filing date of, U.S. Provisional Application No. 63/291,013, filed Dec. 17, 2021, the entirety of which is hereby incorporated by reference herein for all purposes.

BACKGROUND

Tumor Treating Fields (TTFields) therapy is a proven approach for treating tumors using alternating electric fields at frequencies between 50 KHz-1 MHz. The alternating electric fields are induced by electrode assemblies (e.g., arrays of capacitively coupled electrodes, also called transducer arrays) placed on opposite sides of the subject's body. When an AC voltage is applied between opposing electrode assemblies, an AC current is coupled through the electrode assemblies and into the subject's body. And higher currents are strongly correlated with higher efficacy of treatment.

FIG. 1A is a schematic representation of a prior art electrode assembly 40 including nine prior art electrode elements, labeled X1-X9. FIG. 1B is a cross sectional schematic view of electrode elements X7-X9 of the electrode assembly 40, taken along the dashed line in FIG. 1A.

As shown in FIG. 1B, electrode element X7 (taken as exemplary) includes a metal layer (shown with diagonal hatching) and a ceramic (dielectric) layer. A respective layer of electrically conductive hydrogel is provided between each ceramic layer and the subject's skin, to ensure good electrical contact of the electrode elements with the body. An AC voltage from an AC voltage generator (not shown) is applied to the metal layers of electrode elements in opposing electrode assemblies to generate the TTFields in the subject's body. In order to retain the electrode assembly in place during use, an adhesive cover (bandage) is typically provided over the electrode assembly.

During use, the hydrogel and the skin under the electrode elements heat up, and safety considerations require that the skin temperature remain below a safety threshold (e.g., 41° C.). Because the vast majority of the heat appears immediately below the electrode elements X1-X9 (as shown in FIGS. 1C and 1D), the prior art electrode assembly has hot spots immediately below the electrode elements, and cooler regions positioned between the electrode elements. And those hot spots limit the amount of current that can be delivered through the prior art electrode assemblies.

The hydrogel layer(s) of the electrode assembly can also present various issues. For example, since the hydrogel has a limited shelf-life, moisture barrier packaging is required, increasing the cost of packaging for the electrode assembly. Additionally, the signal through the hydrogel can vary with the specific moisture content within the hydrogel, and the hydrogel can fail with either too much or too little water. Further, during use, electrode assemblies having hydrogel layers must be changed out frequently, and many patients have adverse reactions (e.g., allergic reactions) to the hydrogel.

The electrically conductive hydrogel typically has a shorter lifespan than the rest of the electrode assembly. However, the hydrogel is typically integral to the electrode assembly. Thus, upon expiration or contamination of the hydrogel, the entire electrode assembly must be disposed of and replaced.

SUMMARY

Disclosed herein, in one aspect, is an apparatus comprising a subassembly comprising at least one electrode element having a skin-facing side and a skin-facing surface. A skin contact layer can comprise a conductive adhesive. The skin contact layer can be coupled to the subassembly and can be disposed on the skin-facing side of the at least one electrode element. The conductive adhesive can be electrically coupled to the electrode and configured to contact skin of a subject. At least a portion of the skin contact layer can be selectively removable from the subassembly.

A method can comprise coupling, to a subassembly comprising at least one electrode element having a skin-facing side and a skin-facing surface, a skin contact layer comprising a conductive adhesive so that the skin contact layer is disposed on the skin-facing side of the at least one electrode element.

A method can comprise removing a skin contact layer from an assembly, the assembly can comprise at least one electrode element having a skin-facing surface. The assembly can further comprise a plurality of conductive adhesive layers comprising: an outermost conductive adhesive layer that defines the skin contact layer; and at least one intermediate layer disposed between the at least one electrode element and the skin contact layer. Removing the skin contact layer from the assembly can comprise removing the skin contact layer from the at least one intermediate layer, thereby exposing the at least one intermediate layer to define a new skin contact layer.

BRIEF DESCRIPTION OF THE DRAWINGS

Various embodiments are described in detail below with reference to the accompanying drawings, wherein like reference numerals represent like elements.

DETAILED DESCRIPTION

This application describes exemplary electrode assemblies that can be used, e.g., for delivering TTFields to a subject's body and treating one or more cancers or tumors located in the subject's body.

The present invention can be understood more readily by reference to the following detailed description, examples, drawings, and claims, and their previous and following description. However, it is to be understood that this invention is not limited to the specific apparatuses, devices, systems, and/or methods disclosed unless otherwise specified, and as such, of course, can vary.

Headings are provided for convenience only and are not to be construed to limit the invention in any manner. Embodiments illustrated under any heading or in any portion of the disclosure may be combined with embodiments illustrated under the same or any other heading or other portion of the disclosure.

Any combination of the elements described herein in all possible variations thereof is encompassed by the invention unless otherwise indicated herein or otherwise clearly contradicted by context.

As used in the specification and the appended claims, the singular forms "a," "an" and "the" include plural referents unless the context clearly dictates otherwise.

The electrically conductive hydrogel typically has a shorter lifespan than the rest of the electrode assembly. However, removal and replacement of the current hydrogel skin contact layer is not feasible. Thus, upon expiration or contamination of the hydrogel, the entire electrode assembly is disposed of and replaced. What is needed is an electrode assembly that enables removal and replacement of the skin contact layer, and methods related thereto.

Disclosed herein are apparatuses, systems, and methods for adding, removing, or changing a skin contact layer of an apparatus to provide an electrode assembly with a fresh skin contact layer. In this way, as a skin contact layer degrades (e.g., from exposure to air, dirt, oil, etc. from the patient) or is contaminated or potentially contaminated, or otherwise undesired, the skin contact layer can be changed. As can be understood, degradation of the skin contact layer can lead to lower adhesion, lower electrical conductivity, and/or lower thermal conductivity.

Figure 2:
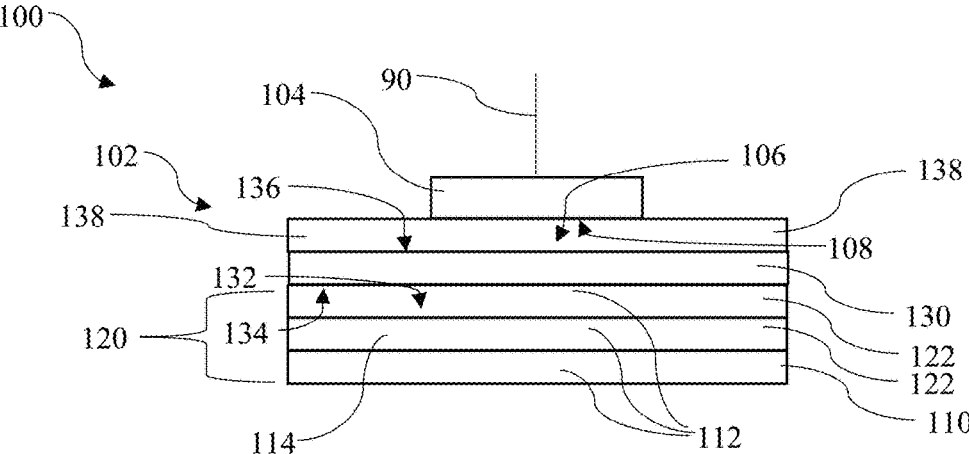
FIG. 2 is a side schematic view of an electrode assembly as disclosed herein.

Referring to FIG. 2, an apparatus 100 can comprise a subassembly 102 comprising at least one electrode element 104. Each electrode element 104 can have a skin-facing (front-facing) side 106 and a skin-facing surface 108. A skin contact layer 110 can be coupled to the subassembly 102 and can be disposed on the skin-facing side of the at least one electrode element 104. The skin contact layer 110 can comprise a conductive adhesive 112 that can be electrically coupled to the electrode and can be configured to contact skin of a subject. For all embodiments disclosed herein, the skin contact layer is optionally a biocompatible conductive adhesive.

In some optional aspects, a first adhesive 114 can couple the skin contact layer 110 to the subassembly 102.

In some aspects, the apparatus 100 can comprise a plurality of layers 120, each comprising the conductive adhesive 112. The plurality of layers 120 can comprise an outermost layer that forms the skin contact layer 110 and one or more intermediate layers 122 disposed between the at least one electrode element 104 and the skin contact layer. The skin contact layer 110 can be coupled to the one or more intermediate layers 122. The skin contact layer 110 can be configured to be decoupled from the one or more intermediate layers 122. In this way, the skin contact layer 110 can be removed from the subassembly, thereby exposing the immediately adjacent intermediate layer 122 that can serve as a skin contact layer. That is, upon decoupling the skin contact layer from the intermediate layer(s), the adjacent intermediate layer can be configured to form an outermost skin contact layer. In some optional aspects, apparatus 100 can comprise a plurality of intermediate layers 122 that are configured to sequentially form the outermost skin contact layer upon separation of respective adjacent layers of conductive adhesive of the plurality of layers of conductive adhesive from the subassembly 102. For example, the apparatus 100 can comprise, 1, 2, 3, 4, 5, 6, 7, 8, 9, 10 or more intermediate layers 122. In some optional aspects, the intermediate layer(s) 122 and the skin contact layer 110 can cooperate to define a total resistance that is less than 15 ohms when measured at a frequency between 50 KHz and 1 MHz. Optionally, one or more layers of the plurality of layers 120 of conductive adhesive can include an inserted release tab on one or more peripheral edge(s) to facilitate removal of a layer. The release tab can be, for example, a portion of thin polymeric film or portion of a release liner.

In some aspects, the skin contact layer 110 can comprise a conductive adhesive composite as described herein. In further aspects, the skin contact layer 110 can comprise a hydrogel.

In some optional aspects, the subassembly 102 can further comprise a layer of anisotropic material 130 having a skin-facing (front-facing) side 132, a skin-facing surface 134, and an opposing outwardly facing (rear-facing) surface 136. The electrode element(s) 104 can be in electrical contact with the outwardly facing surface 136 of the layer of anisotropic material 130. The skin contact layer 110 can be disposed on the skin-facing side 132 of the layer of anisotropic material 130. In some embodiments, the skin contact layer 110 can be disposed on the skin-facing surface 134 of the layer of anisotropic material 130. In use, it is contemplated that the layer of anisotropic material can aid in avoiding or reducing overheating of the electrodes and associated discomfort on the skin by dissipating both electrical current and heat in a lateral (in-plane) direction rather than passing directly through the layer (in a direction perpendicular to the plane of the skin contact layer) in a concentrated manner. Optionally, the assembly 100 can comprise a conductive material 138 disposed between the anisotropic material 130 and the electrode element(s) 104. In some embodiments, the anisotropic material 130 can be disposed between, and in contact with, the conductive material 138 and the skin contact layer 110. In further aspects, the anisotropic material 130 and/or the conductive material 138 can be omitted.

The figures (e.g. FIG. 2) further illustrate a lead 90 which supplies an AC voltage (directly or indirectly) from an AC voltage generator (not shown) to the electrode element(s) to generate the TTFields when the electrode assembly 100 is affixed to the subject's body for treatment.

Figure 6A:
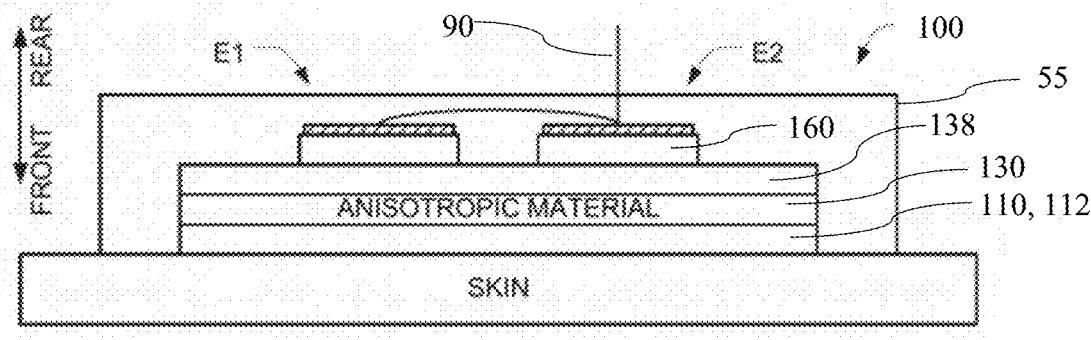
FIG. 6A is a cross sectional representation of another embodiment including electrode elements E1, E2, taken along the dashed line in FIG. 5.
Figure 7:
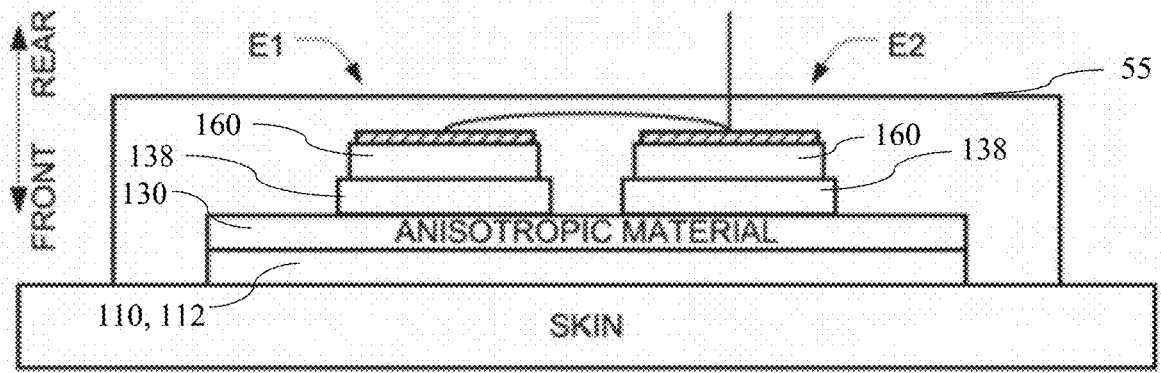
FIG. 7 is a cross sectional representation of yet another embodiment including electrode elements E1, E2, taken along the dashed line in FIG. 5.

Optionally, the electrodes 104 can comprise dielectric (e.g., ceramic) material 160 (see, for example, FIG. 6A and FIG. 7).

Methods of Adding One or More Skin Contact Layers

Figure 3:
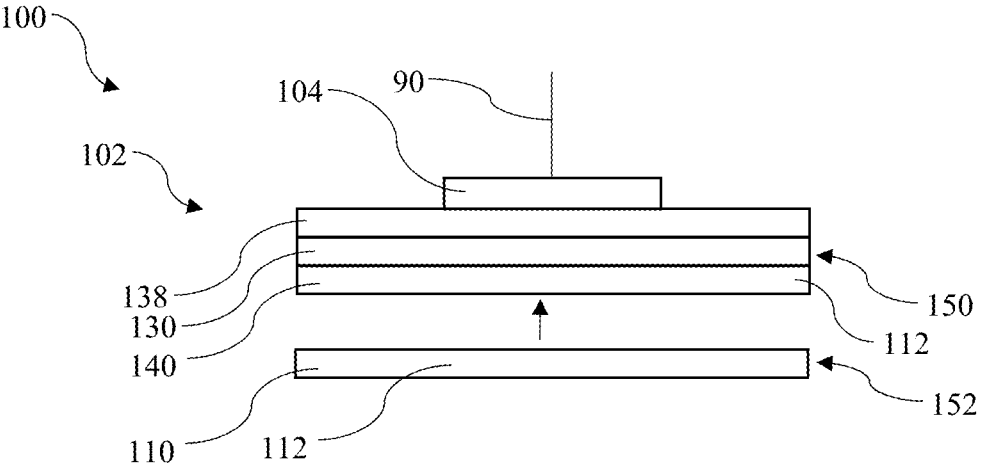
FIG. 3 is a side schematic view of an electrode assembly receiving a skin contact layer.

Referring to FIG. 2 and FIG. 3, a subassembly 102 of apparatus 100 can comprise at least one electrode element 104 having the skin-facing side 106 and the skin-facing surface 108. A method can comprise coupling, to the subassembly 102, a skin contact layer 110 comprising a conductive adhesive 112 so that the skin contact layer is disposed on the skin-facing side of the at least one electrode element.

For example, the subassembly 102 can comprise, prior to coupling of the skin contact layer 110, a pre-existing (e.g., an old, used, or otherwise undesired) skin contact layer 140, and the skin contact layer 110 can be coupled to the preexisting skin contact layer 140. In further aspects, prior to coupling the skin contact layer 110, the subassembly 102 does not have a pre-existing skin contact layer thereon. For example, the subassembly 102 can comprise one or more electrode elements 104, optionally, an anisotropic layer 130, and optionally, a conductive layer 138 between the anisotropic layer and the electrode element(s). It is contemplated that additional layers comprising conductive adhesive 112 can be sequentially coupled to the subassembly, sequentially forming skin contact layers 110. In some optional aspects, additional layers can be added until the intermediate layer(s) 122 and the skin contact layer 110 can cooperate to define a total resistance that surpasses 15 ohms when measured at a frequency between 50 KHz and 1 MHz.

In these, and other embodiments described herein, the electrode(s) 104 optionally can comprise a layer of dielectric (e.g., ceramic) material.

In further optional aspects, the pre-existing skin contact layer 140 can be removed prior to coupling the skin contact layer 110. In this way, the electrical and thermal resistances of the pre-existing skin contact layer 140 can be removed.

In some aspects, the subassembly 102 can comprise a layer of anisotropic material 130 having a skin-facing (front-facing) side 132, a skin-facing surface 134, and an opposing outwardly facing (rear-facing) surface 136, as discussed above. The electrode element(s) 104 can be in electrical contact with the outwardly facing surface 136 of the layer of anisotropic material 130. The skin contact layer 110 can be disposed on the skin-facing side 132 of the layer of anisotropic material 130. In some embodiments, the skin contact layer 110 can be disposed on the skin-facing surface 134 of the layer of anisotropic material 130. Optionally, the assembly 100 can comprise a conductive material 138 disposed between the anisotropic material 130 and the electrode element(s) 104. In some embodiments, the anisotropic material 130 can be disposed between, and in contact with, the conductive material 138 and the skin contact layer 110. In further aspects, the anisotropic material 130 and/or the conductive material 138 can be omitted.

In some aspects, the layer of anisotropic material 130 and the skin contact layer 110 can define respective circumferential edges 150, 152. It can be advantageous for the circumferential edge 152 of the skin contact layer to align with the circumferential edge 150 of the layer of anisotropic material 130 in order to avoid hotspots of high current, temperature, electric fields, etc. Accordingly, in some aspects, the method can further comprise trimming the circumferential edge 152 of the skin contact layer 110 to align with the circumferential edge 150 of the layer of anisotropic material. For example, for an anisotropic material 130 having a circular profile, the circumferential edge 152 can be trimmed so that the skin contact layer is concentric with, and has the same or substantially the same diameter as, the layer of anisotropic material 130. Thus, prior to trimming, the skin contact layer 110 can have a greater surface area than the anisotropic material 130 in order to provide sufficient material to trim. Optionally, the circumferential edge 152 can be trimmed prior to coupling the skin contact layer 110 to the subassembly 102. In further aspects, the circumferential edge 152 can be trimmed after coupling the skin contact layer 110 to the subassembly 102.

In further aspects, a jig can be used to align the circumferential edge 152 of the skin contact layer 110 with the circumferential edge 150 of the layer of anisotropic material 130.

In various aspects, and as further described herein, the skin contact layer 110 can comprise a conductive adhesive composite or a hydrogel. In an embodiment, the added skin contact layer is, or comprises, a conductive adhesive composite having an in-plane conductivity (x-y plane) that is substantially equal to the conductivity in directions perpendicular to the plane of the layer (z-direction). That is, neither conductivity exceeds the other by 1.5 times or greater. In another embodiment, the added skin contact layer is a conductive adhesive composite having an in-plane conductivity (x-y plane) that is at least two times greater than the conductivity in directions perpendicular to the plane of the layer (z-direction). In other aspects, the added skin contact layer is a conductive adhesive composite having an in-plane conductivity (x-y plane) that is from about 1.5 times to about 2 times greater than the conductivity in directions perpendicular to the plane of the layer (z-direction).

In some aspects, a method can comprise coupling, to the subassembly 102, a plurality of layers comprising a skin contact layer 110 (which may comprise a conductive adhesive 112) so that the plurality of layers comprising the skin contact layer is disposed on the skin-facing side of the at least one electrode element, and such that the skin contact layer becomes the outermost skin contact layer. The plurality of layers may comprise two layers, or three layers, or more than three layers. For example, the two layer addition may comprise a layer of anisotropic material 130 and a skin contact layer 110; and the three layer addition may comprise a layer of the conductive material 138, a layer of anisotropic material, and a skin contact layer. In all of these embodiments, either or both of the skin contact layer 110 and the layer of the conductive material 138 may be, or comprise, a conductive adhesive 112, such as a conductive adhesive composite, as discussed herein. In all of these aspects, other embodiments of the subassembly 102 and methods of coupling the skin contact layer 110 (or the plurality of layers comprising the skin contact layer) to the subassembly, as described herein, may also be appropriate in forming additional embodiments.

Once the skin contact layer 110 is applied to the subassembly 102, the skin contact layer 110 can be applied to a patient, and the apparatus 100 can then be used to apply TTFields to a target area of a patient. Before or upon expiration (e.g., expiration from degradation) of the skin contact layer 110, a new skin contact layer can be applied to the subassembly 102 (which may be in the form of a plurality of layers comprising a skin contact layer, as described above), and the new skin contact layer can be applied to the same or a different patient, and the apparatus 100 can then be used to apply TTFields to a target area of said patient.

Figure 4:
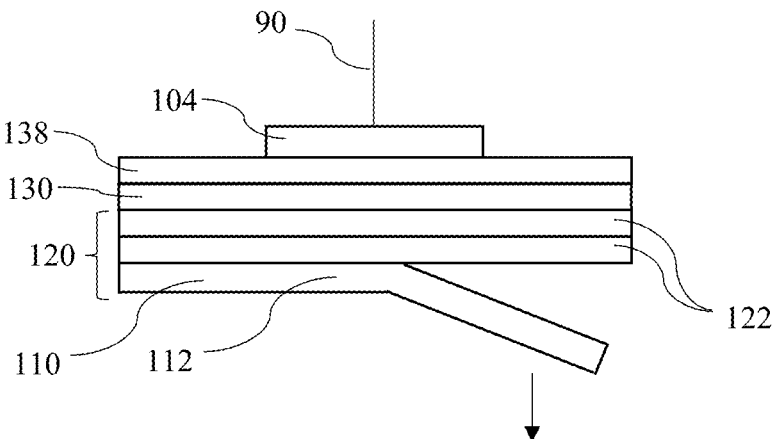
FIG. 4 is a side schematic view of an electrode assembly having a skin contact layer removed.

In another aspect, a kit may be provided including sets comprising any number of the plurality of layers comprising a skin contact layer, as described above. For example, a two layer unit may comprise a layer of anisotropic material 130 and a skin contact layer 110; and a three layer unit may comprise a layer of the conductive material 138, a layer of anisotropic material, and a skin contact layer. In each unit (a two layer unit or a three layer unit), the outward facing adhesive surface (or surfaces) may be protected by a release layer (or release layers). Accordingly, a subject utilizing the electrode assemblies may have a ready supply of multiple replacement units to renew a skin contact layer as needed.
Methods of Removing One or More Skin Contact Layers Referring to FIGS. 2 and 4, the assembly 100 can comprise at least one electrode element 104 having a skin-facing surface 108. The assembly 100 can comprise a plurality of layers 120 comprising conductive adhesive 112 (conductive adhesive layers). The plurality of conductive adhesive layers 120 can comprise an outermost conductive adhesive layer that defines the skin contact layer 110 and at least one intermediate layer 122 disposed between the at least one electrode element and the skin contact layer 110. Optionally, one or more layers of the plurality of layers 120 of conductive adhesive can include an inserted release tab on one or more peripheral edge(s) to facilitate removal of a layer. The release tab can be, for example, a portion of thin polymeric film or a portion of a release liner.

A method can comprise removing the skin contact layer 110 from the at least one intermediate layer 122, thereby exposing the at least one intermediate layer to define a new skin contact layer. For example, upon removing the skin contact layer 110 from the at least one intermediate layer 122, the at least one intermediate layer can be configured to form an outermost skin contact layer.

In some optional aspects, the apparatus 100 can comprise a plurality of intermediate layers 122 that are configured to sequentially form the (outermost) skin contact layer 110 upon separation of respective adjacent (outermost) conductive adhesive layers of the plurality of conductive adhesive layers 120 from the assembly.

In some optional aspects, the assembly 100 can further comprise a layer of anisotropic material 130 having a skin-facing side 132, a skin-facing surface 134, and an opposing outwardly facing surface 136, as discussed above. The at least one electrode element 104 can be in electrical contact with the outwardly facing surface 136 of the layer of anisotropic material 130, and the skin contact layer can be disposed on the skin-facing side 132 of the layer of anisotropic material 130. In some embodiments, the skin contact layer 110 can be disposed on the skin-facing surface 134 of the layer of anisotropic material 130. Optionally, the assembly 100 can comprise a conductive material 138 disposed between the anisotropic material 130 and the electrode element(s) 104. In some embodiments, the anisotropic material 130 can be disposed between, and be in contact with, the conductive material 138 and the skin contact layer 110. In further aspects, the anisotropic material 130 and/or the conductive material 138 can be omitted.

In some aspects, the plurality of conductive adhesive layers 120 can comprise a conductive adhesive composite (e.g., a conductive adhesive composite as disclosed herein) or hydrogel.

In some aspects, a method can comprise removing the skin contact layer 110 (or the plurality of layers comprising a skin contact layer, as described above) from the at least one intermediate layer 122, thereby exposing the at least one intermediate layer to define a new skin contact layer. The plurality of layers may comprise two layers, or three layers, or more than three layers. For example, the two layer unit to be removed may comprise a layer of anisotropic material 130 and a skin contact layer 110; and the three layer unit to be removed may comprise a layer of the conductive material

138, a layer of anisotropic material, and a skin contact layer. In all of these embodiments, either or both of the skin contact layer 110 and the layer of the conductive material 138 may be a conductive adhesive 112, such as a conductive adhesive composite, as discussed herein. In all of these aspects, other embodiments of the subassembly 102 and methods of removing the skin contact layer 110 (or the plurality of layers comprising the skin contact layer) from the at least one intermediate layer 122, as described herein, may also be appropriate in forming additional embodiments.

Once the skin contact layer 110 is removed (or the plurality of layers comprising a skin contact layer, as described above, is removed) to expose a (new) outermost skin contact layer, the outermost skin contact layer can be applied to a patient, and the apparatus 100 can then be used to apply TTFields to a target area of a patient. Before or upon expiration (e.g., expiration from degradation) of the outermost skin contact layer, the outermost skin contact layer can be removed to expose the adjacent skin contact layer. The adjacent skin contact layer can then be applied to the same or a different patient, and the apparatus 100 can then be used to apply TTFields to a target area of said patient. Optionally, after removal of a skin contact layer 110 (or after removal of the plurality of layers comprising a skin contact layer), a new replacement skin contact layer 110 (or plurality of layers comprising a skin contact layer) may be added in its place.
Exemplary Configurations The following provide exemplary configurations of the apparatuses and methods disclosed herein.

Figure 5:
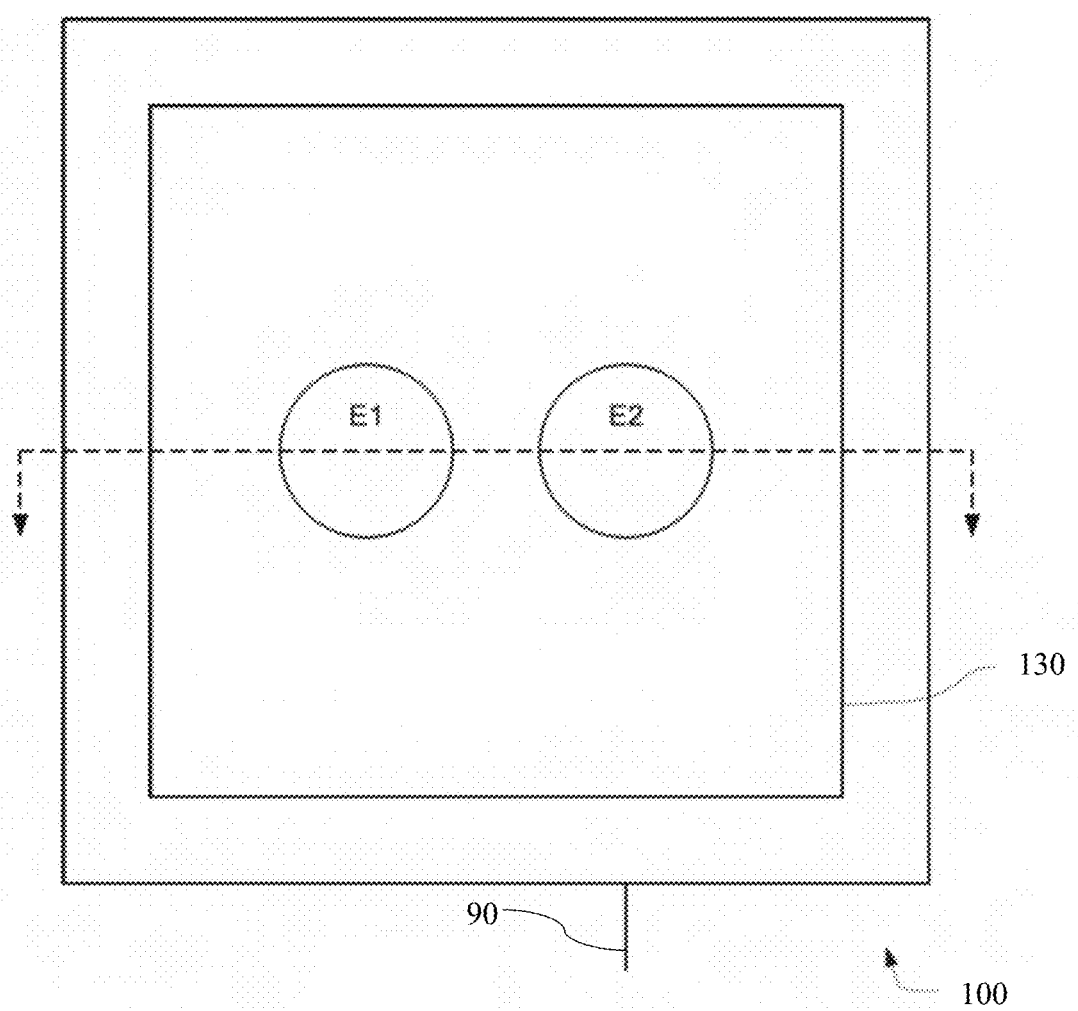
FIG. 5 is a plan schematic representation of an electrode assembly including electrode elements E1, E2, that is used for applying TTFields to a subject's body.

FIG. 5 is a schematic representation of an electrode assembly (e.g., apparatus 100) of an embodiment including electrode elements used for applying TTFields to a subject's body. In FIG. 5, only two electrode elements labeled E1 and E2 are shown, but in other optional aspects, it is contemplated that additional electrode elements can be included in the electrode assembly. In alternative embodiments, the electrode assembly includes only a single electrode element. Notably, FIG. 5 depicts an electrode assembly generically, and those electrode assemblies E1 and E2 can have different configurations (e.g., as described below in connection with FIGS. 6A-9).

FIG. 6A is a cross sectional representation of a first embodiment of an electrode assembly 100 including electrode elements E1, E2, taken along the dashed line in FIG. 5.

In the FIG. 6A embodiment, the electrode assembly 100 includes a sheet of anisotropic material 130 having a front face (facing towards the subject's skin in FIG. 6A) and a rear face. This sheet has a first thermal conductivity in a direction that is perpendicular to the front face. Thermal conductivity of the sheet in directions that are parallel to the front face is more than two times higher than the first thermal conductivity. In some preferred embodiments, the thermal conductivity of the sheet in directions that are parallel to the front face is more than ten times higher than the first thermal conductivity. The sheet in the FIG. 6A embodiment is also anisotropic in another respect. More specifically, the sheet has a first resistance in a direction that is perpendicular to the front face, and the resistance of the sheet in directions that are parallel to the front face is less than half of the first resistance. In some embodiments, the resistance of the sheet in directions that are parallel to the front face is less than 10% of the first resistance.

In some embodiments, the sheet of anisotropic material 130 is a sheet of graphite. In some embodiments, the sheet of anisotropic material 130 is a sheet of synthetic graphite, such as pyrolytic graphite (for example, Pyrolytic Graphite Sheet (PGS), available from Panasonic Industry, Kadoma, Osaka, Japan). In other embodiments, the sheet of anisotropic material is graphite foil made from compressed high purity exfoliated mineral graphite (e.g., MinGraph® 2010A Flexible Graphite, available from Mineral Seal Corp., Tucson, Arizona, USA); or graphitized polymer film, e.g., graphitized polyimide film, (including, but not limited to, that supplied by Kaneka Corp., Moka, Tochigi, Japan). In other embodiments, the anisotropic material can be pyrolytic carbon. Other embodiments can utilize sheets of other conducting materials with anisotropic properties. In some embodiments (e.g., when the sheet of anisotropic material is a sheet of pyrolytic graphite), the sheet of anisotropic material is nonmetallic.

The electrode assembly of FIG. 6A further includes a skin contact layer 110 of conductive adhesive 112 disposed on the front face of the sheet of anisotropic material 130. The skin contact layer of conductive adhesive is configured to ensure good electrical contact between the device and the body. In some embodiments, the skin contact layer can cover the entire front face of the sheet of anisotropic material. For example, the skin contact layer can be the same size or larger than the sheet of anisotropic material. In some embodiments, the skin contact layer of conductive adhesive comprises hydrogel. In these embodiments, the hydrogel can have a thickness between 50 μm and 2000 μm. In other embodiments, the skin contact layer of conductive adhesive comprises a conductive adhesive composite as further disclosed herein.

The electrode assembly of FIG. 6A further includes a first electrode element E1 positioned behind the sheet. The first electrode element E1 has a first front face disposed in electrical contact with the rear face of the sheet 130. In the FIG. 6A embodiment, the first electrode element E1 includes a first layer of dielectric (e.g., ceramic) material 160 having a front face and a rear face, and a first layer of metal (shown with diagonal hatching) disposed on the rear face of the first layer of dielectric material. The front face of the first layer of dielectric material is the first front face of the first electrode element E1.

The electrode assembly of FIG. 6A further includes a first layer of conductive material 138 positioned between the first front face of the first electrode element E1 (i.e., the front face of the first layer of dielectric material) and the rear face of the sheet of anisotropic material 130. The first layer of conductive material facilitates the electrical contact between the first front face of the first electrode element E1 and the rear face of the sheet. In the illustrated embodiment, the layer of conductive material 138 can be a layer of hydrogel. But in alternative embodiments, a different conductive material (e.g., conductive grease, conductive adhesives, conductive tape, etc.) could be used. For example, the layer of conductive material can comprise a conductive adhesive composite as further disclosed herein.

The electrode assembly can optionally include one or more additional electrode elements. In the illustrated embodiment, the electrode assembly includes a second electrode element E2 positioned behind the sheet. The second electrode element E2 has a second front face disposed in electrical contact with the rear face of the sheet 130. The two electrode elements E1, E2 in FIG. 6A have identical structures. Thus, the second electrode element E2 includes a second layer of dielectric (e.g., ceramic) material having a front face and a rear face, and a second layer of metal disposed on the rear face of the second layer of dielectric material. The front face of the second layer of dielectric material is the second front face of the second electrode element E2.

The first layer of conductive material 138 is positioned between the second front face of the second electrode element E2 (i.e., the front face of the second layer of dielectric material) and the rear face of the sheet 130. The first layer of conductive material facilitates the electrical contact between the second front face of the second electrode element E2 and the rear face of the sheet. As described for E1, the conductive material 138 in FIG. 6A can be a layer of hydrogel, but in alternative embodiments, a different conductive material can be used (e.g., conductive grease, conductive adhesives, conductive tape, etc.). For example, the layer of conductive material can comprise a conductive adhesive composite as further disclosed herein.

The metal layers of all of the electrode elements (i.e., E1 and E2 in the illustrated embodiment), can be wired together (e.g., using wires, traces on a flex circuit, etc.) to a lead 90. The lead 90 supplies an AC voltage from an AC voltage generator (not shown) to the electrode elements 104 to generate the TTFields when the electrode assembly 100 is affixed to the subject's body for treatment.

Figure 8:
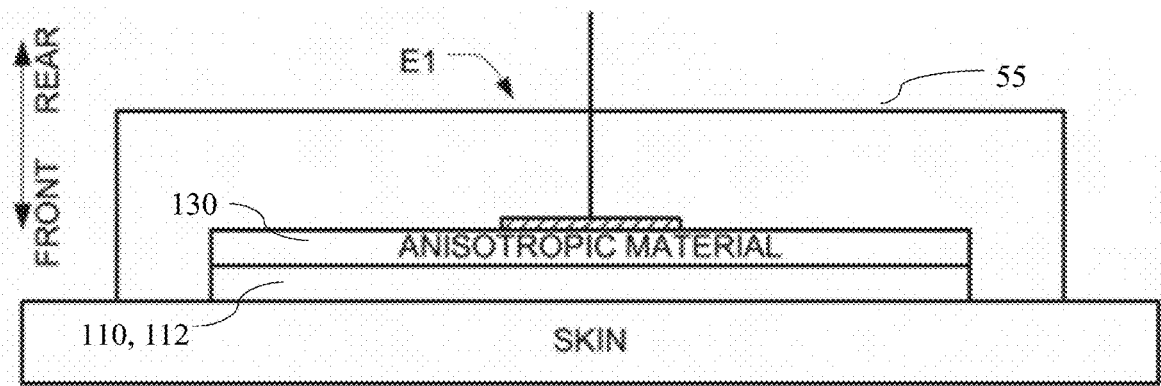
FIG. 8 is a cross sectional representation of still another embodiment that includes a single electrode element E1.

Optionally, for all of the embodiments disclosed herein, the electrode assembly can include a flexible self-adhesive backing 55 (as shown in FIGS. 6A, 7 and 8) configured to support the sheet of anisotropic material 130, the first electrode element E1 (and any other electrode elements present in the electrode assembly), and the layer of conductive material 138 so that the skin contact layer of conductive adhesive can be positioned against the subject's skin.

As noted above, FIG. 5 is a plan schematic representation of an electrode assembly including electrode elements E1, E2. This view of FIG. 5 (not to scale) also demonstrates that the area of the sheet 130 can be larger (e.g., at least 10 times larger) than the combined areas of the electrode elements E1, E2. When an AC voltage is applied to the electrode elements E1, E2, heat spreads out across the entire sheet, which minimizes or eliminates hot spots.

Figures 1A, 1B:
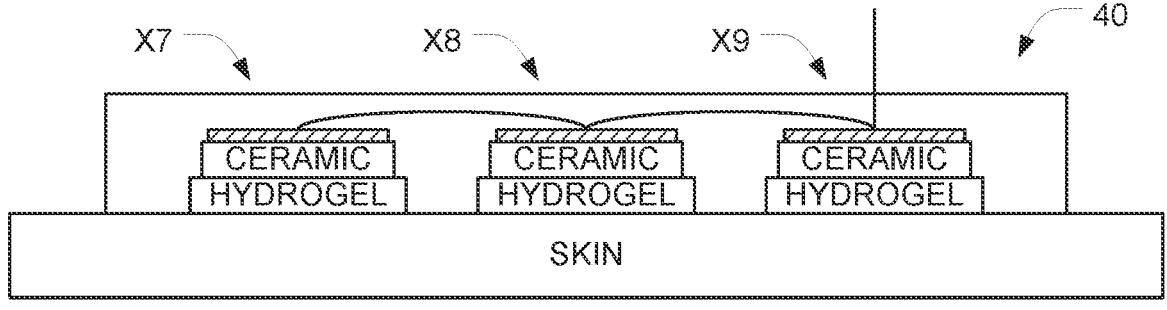
FIG. 1A is a schematic representation of a prior art electrode assembly.
FIG. 1B is a cross sectional view of electrode elements of the prior art electrode assembly, taken along the dashed line in FIG. 1A.
Figure 1C:
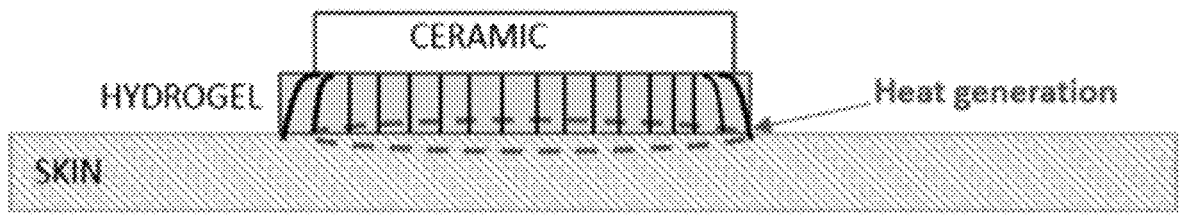
FIG. 1C is a cross sectional view showing the heat generation properties of a prior art electrode element.

This reduction in hot spots (as compared to the prior art) becomes apparent by comparing FIG. 1C to FIG. 6B. More specifically, FIG. 1C shows the current distribution and heat generation for prior art electrode elements, each of which is positioned on a conductive hydrogel layer that is about the same size as the electrode element. As shown in FIG. 1C, all the current passes through the hydrogel layer directly beneath the electrode elements, which results in hot spots directly beneath the electrode elements.

Figure 1D:
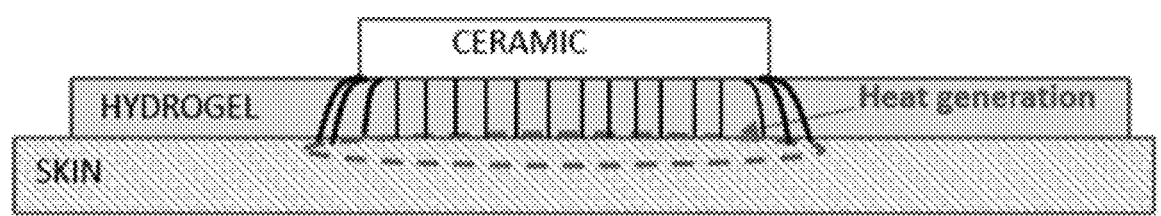
FIG. 1D is a cross sectional view showing the heat generation properties of a hypothetical modification to the FIG. 1B electrode element.

One might initially think that this problem could be solved by increasing the area of the hydrogel to cover all the regions between the electrode elements. But this is not the case. More specifically, FIG. 1D shows the current distribution and heat generation for this hypothetical electrode assembly. As shown in FIG. 1D, all the current still passes through the hydrogel layer directly beneath the electrode elements, which results in hot spots directly beneath the electrode elements.

Figure 6B:
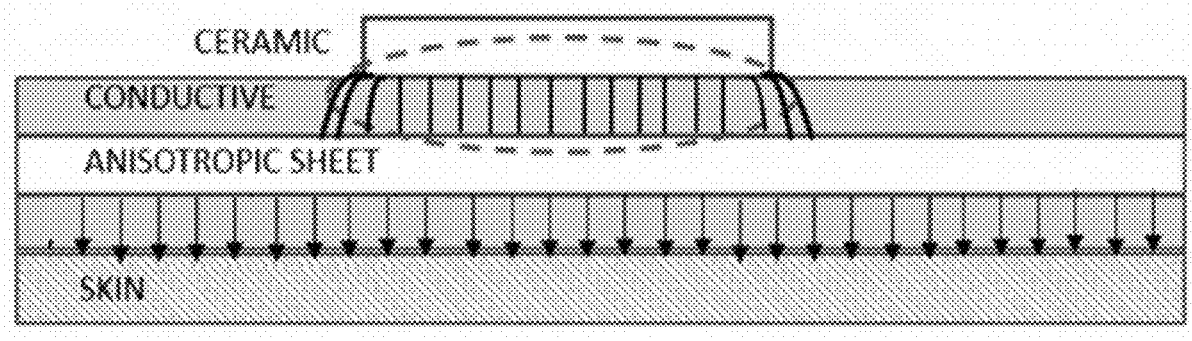
FIG. 6B is a cross sectional view showing the heat generation properties of the FIG. 6A embodiment.

In contrast, FIG. 6B shows the current distribution for the FIG. 6A embodiment. As shown in FIG. 6B, the current is still distributed in the upper hydrogel layer only in the area below the electrode element. However, the sheet of anisotropic material spreads the heat out across its entire area because the thermal conductivity in the horizontal directions (i.e., in directions parallel to the face of the sheet) is much higher than its thermal conductivity in the vertical direction. In addition to spreading out the heat, the low electrical resistance of the sheet in the horizontal direction spreads the current outward throughout the sheet, and this spread-out current distribution continues in the skin contact layer of conductive adhesive, and thence to the subject's skin. Because the current and heat in this embodiment are both spread out over a larger area of the skin contact layer of conductive adhesive 110, hotspots are eliminated (or at least minimized). This means that for a given applied AC voltage, the hottest point beneath the electrode assembly of the FIG. 6A/B embodiment will be lower than the hottest point beneath the electrode assembly of the FIG. 1 prior art embodiment. Accordingly, the current can be increased (with respect to the prior art current) without exceeding the safety temperature threshold at any point beneath the electrode assembly of the FIG. 6A embodiment. And this increase in current will advantageously increase the efficacy of the TTFields treatment. Similar results can be achieved when the hydrogel is replaced with a conductive adhesive such as the conductive adhesive composite as disclosed herein.

FIG. 7 is a cross sectional representation of a second embodiment of an electrode assembly 100 including electrode elements E1, E2, taken along the dashed line in FIG. 5. The FIG. 7 embodiment is similar to the FIG. 6A embodiment in all respects except as follows. The FIG. 6A embodiment includes a large continuous layer of conductive material 138 (e.g., hydrogel or conductive adhesive composite) positioned between the sheet of anisotropic material and the front faces of both the first and second electrode elements E1 and E2. In contrast, the FIG. 7 embodiment includes a separate region of conductive material 138 for each individual electrode element. Thus, the FIG. 7 embodiment includes a first layer of conductive material 138 positioned between the first front face of the first electrode element E1 and the rear face of the sheet 130, and also includes a second layer of conductive material 138 positioned between the second front face of the second electrode element E2 and the rear face of the sheet. The first and second layers of conductive material facilitate the electrical contact between the respective electrode front faces and the rear face of the sheet 130. (FIG. 7, like FIG. 6A, illustrates electrodes E1 and E2 comprising a metal backing layer (diagonal hatching) and a dielectric layer 160). In some embodiments, the layers of conductive material 138 can be layers of hydrogel, but in alternative embodiments, different conductive materials (e.g., conductive grease, conductive adhesives, conductive tape, etc.) can be used. For example, the layers of conductive material can be layers of conductive adhesive composite as disclosed herein.

In some aspects, the skin contact layer 110 can comprise a conductive adhesive 112 (FIG. 7), such as a conductive adhesive composite as described herein. In further aspects, the skin contact layer 110 can comprise a hydrogel.

As in the FIG. 6A embodiment, the current in the FIG. 7 embodiment is still concentrated in the upper layers of conductive material only in the areas below the electrode elements. The sheet of anisotropic material 130 spreads out the heat and the current as described above in connection with the FIG. 6A embodiment, which eliminates or at least minimizes hot spots. This means that for a given applied AC voltage, the hottest point beneath the electrode assembly of the FIG. 7 embodiment will be lower than the hottest point beneath the electrode assembly of the FIG. 1 prior art embodiment. Accordingly, the current can be increased (with respect to the prior art current) without exceeding the safety temperature threshold at any point beneath the electrode assembly of the FIG. 5 embodiment. And this increase in current will advantageously increase the efficacy of the TTFields treatment.

FIG. 2 is a cross sectional representation of a third embodiment of an electrode assembly that includes a single electrode element. In the FIG. 2 embodiment, as described above, the electrode assembly includes a sheet of anisotropic material 130 having a front face (facing towards the subject's skin in FIG. 2) and a rear face. This sheet is similar to the sheet described above in connection with FIG. 6A. In some embodiments, the sheet of anisotropic material is a sheet of pyrolytic graphite. In other embodiments, the sheet of anisotropic material is graphite foil made from compressed high purity exfoliated mineral graphite. In other embodiments, the sheet of anisotropic material is graphitized polymer film, e.g., graphitized polyimide film. In other embodiments, the sheet of anisotropic material is a sheet of pyrolytic carbon. In other embodiments, the sheet of anisotropic material is a sheet of another conductive anisotropic material. The FIG. 2 embodiment also illustrates the layer of conductive material 138. The beneficial effects of spreading out the heat and the current as described above in connection with the FIG. 6A embodiment, which eliminates or at least minimizes hot spots, are similarly realized in this third embodiment. This means that for a given applied AC voltage, the hottest point beneath the electrode assembly of the FIG. 2 embodiment will be lower than the hottest point beneath the electrode assembly of the FIG. 1 prior art embodiment. Accordingly, the current can be increased (with respect to the prior art current) without exceeding the safety temperature threshold at any point beneath the electrode assembly of the FIG. 2 embodiment. And this increase in current will advantageously increase the efficacy of the TTFields treatment.

FIG. 8 is a cross sectional representation of a fourth embodiment of an electrode assembly that includes a single electrode element E1. The FIG. 8 embodiment is similar to the FIG. 6 embodiment except that the first front face of the first electrode element E1 is the front face of the piece of metal (shown as diagonal hatching) and is positioned in direct contact with the rear face of the sheet of anisotropic material 130 (instead of including a dielectric layer 160 and being electrically connected via an intervening layer of conductive material 138).

Similar to the FIG. 2 embodiment, the sheet of anisotropic material 130 in the FIG. 8 embodiment spreads out the heat and the current as described above in connection with the FIG. 6A embodiment, which eliminates or at least minimizes hot spots. This means that for a given applied AC voltage, the hottest point beneath the electrode assembly of the FIG. 8 embodiment will be lower than the hottest point beneath the electrode assembly of the FIG. 1 prior art embodiment. Accordingly, the current can be increased (with respect to the prior art current) without exceeding the safety temperature threshold at any point beneath the electrode assembly of the FIG. 8 embodiment. And this increase in current will advantageously increase the efficacy of the TTFields treatment.

In some aspects, the skin contact layer 110 can comprise a conductive adhesive 112 (FIG. 8), such as a conductive adhesive composite as described herein. In further aspects, the skin contact layer 110 can comprise a hydrogel.

In some aspects, a capacitor can be connected in series with and behind the piece of metal.

Figure 9:
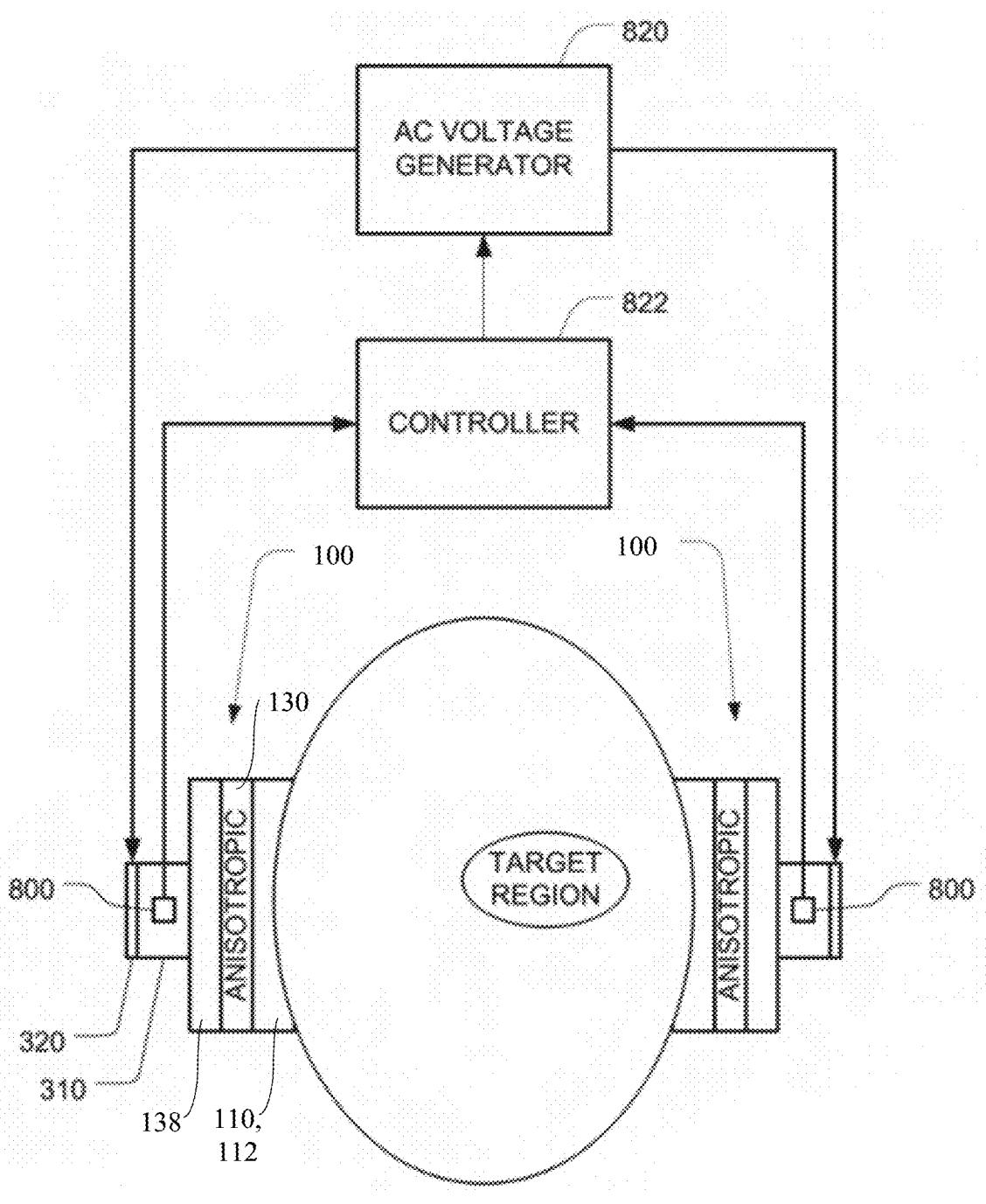
FIG. 9 is a block diagram of a system incorporating two electrode assemblies that is used for applying TTFields to a subject's body.

FIG. 9 shows how a pair of the FIG. 6A electrode assemblies can be used to apply an alternating electric field to a target region in the subject's body. (Note that any of the electrode assemblies described above in connection with FIGS. 2-8 can be used).

The method of applying TTFields includes positioning a first electrode assembly at a first position on or in the subject's body. (In the example depicted in FIG. 9, the first electrode assembly is positioned on the subject's skin at the right of the subject's head facing a target region, e.g., a tumor).

The method also includes positioning a second electrode assembly at a second position in or on the subject's body. (In the example depicted in FIG. 9, the second electrode assembly is positioned on the subject's skin at the left of the subject's head facing the target region).

The method further includes applying an alternating voltage between the first electrode assembly and the second electrode assembly. The applying is performed after positioning the first electrode assembly and the second electrode assembly.

The alternating voltage between the first electrode assembly and the second electrode assembly can be applied by an AC voltage generator 820. In some embodiments, the frequency of the alternating voltage is between 50 kHz and 1 MHz, or between 100 kHz and 500 kHz. In the illustrated example, the AC voltage generator is controlled by a controller 822. The controller 822 can use temperature measurements to control the amplitude of the current to be delivered via the first and second electrode assemblies 100 in order to maintain temperatures below a safety threshold (e.g., 41° C.). This can be accomplished, for example, by measuring a first temperature of the first electrode element, measuring a second temperature of the second electrode element, and controlling the applying of the alternating voltage based on the first temperature and the second temperature, as described below.

FIG. 9 depicts one example of hardware that is suitable for this purpose. More specifically, temperature sensors 800 (e.g., thermistors) are positioned in thermal contact with respective electrode elements (for example, dielectric material 310/layer of metal 320) within each of the electrode assemblies 100. The temperature sensors 800 measure respective first and second temperatures (e.g., at first and second electrode elements in the first electrode assembly and second electrode assembly, respectively), and the controller 822 controls the output of the AC voltage generator 820 based on these temperatures. FIG. 9 also shows the skin-contact layer 110 comprising conductive adhesive 112, the layer of anisotropic material 130, and the layer of conductive material 138 present between electrode elements 310/320 and the layer of anisotropic material 130.

As discussed above, it is contemplated that one or more of the layers of conductive materials (for example, layers 110, 138 comprising conductive adhesive 112) disclosed herein can comprise conductive adhesive composites (described further below) rather than hydrogel. In exemplary aspects, the conductive adhesive composite can comprise a dielectric material and conductive particles dispersed within the dielectric material. In some embodiments, at least a portion of the conductive particles can define a conductive pathway through a thickness of the conductive adhesive composite. It is contemplated that the conductive particles can be aligned in response to application of an electric field such that the conductive particles undergo electrophoresis. In some aspects, the dielectric material of the electrode assemblies is a polymeric adhesive. Optionally, in these aspects, the polymeric adhesive can be an acrylic adhesive. In some aspects, the conductive particles can comprise carbon. Optionally, in these aspects, the conductive particles can comprise graphite powder. Additionally, or alternatively, the conductive particles can comprise carbon flakes. Additionally, or alternatively, the conductive particles can comprise carbon granules. Additionally, or alternatively, the conductive particles can comprise carbon fibers. Additionally, or alternatively, the conductive particles can comprise carbon nanotubes. Additionally, or alternatively, the conductive particles can comprise carbon nanowires. Additionally, or alternatively, the conductive particles can comprise carbon black powder. Additionally, or alternatively, the conductive particles can comprise carbon microcoils. The conductive particles can be any combination of the above types of particles. In further aspects, the conductive adhesive composite further comprises a polar material (e.g., a polar salt). The polar salt can be a quaternary ammonium salt, such as a tetra alkyl ammonium salt. Exemplary conductive adhesive composites, as well as methods for making such conductive adhesive composites, are disclosed in U.S. Pat. Nos. 8,673,184 and 9,947,432, which are incorporated herein by reference for all purposes. In exemplary aspects, the conductive adhesive composite can be a dry carbon/salt adhesive, such as the OMNI-WAVE™ adhesive compositions manufactured and sold by FLEXCON® (Spencer, MA, USA); or, alternatively, ARcare® 8006 electrically conductive adhesive composition manufactured and sold by Adhesives Research, Inc. (Glen Rock, PA, USA).

In exemplary aspects, by using a conductive adhesive composite as a skin contact layer as disclosed herein, it is contemplated that additional backing and/or cover layers (such as, for example self-adhesive backing 55) can be omitted. In these aspects, it is contemplated that the conductive adhesive composite can provide sufficient adhesion to the skin such that it is unnecessary to provide additional layers to maintain a desired position of the electrode assembly on the body of the subject, thereby improving ease of use and decreasing the overall cost of manufacture and use.

In further aspects, by avoiding the use of hydrogel within an electrode assembly, it is contemplated that electrode assemblies comprising conductive adhesive composites as disclosed herein do not require moisture barrier packaging, thereby making the cost of packaging far more affordable. Additionally, it is contemplated that the conductive adhesive composites of the disclosed electrode assemblies can avoid the signal variation issues of hydrogels, thereby providing consistent material properties (e.g., tackiness) and reliable performance during delivery of TTFields. Further, it is contemplated that the disclosed conductive adhesive composites can have a far greater shelf life than hydrogels, thereby decreasing the frequency at which electrode assemblies (or the skin contact layers of electrode assemblies) must be replaced.

Exemplary Aspects

In view of the described products, systems, and methods and variations thereof, herein below are described certain more particularly described aspects of the invention. These particularly recited aspects should not however be interpreted to have any limiting effect on any different claims containing different or more general teachings described herein, or that the "particular" aspects are somehow limited in some way other than the inherent meanings of the language literally used therein.

Aspect 1: An apparatus comprising:
a subassembly comprising at least one electrode element having a skin-facing side and a skin-facing surface; and
a skin contact layer comprising a conductive adhesive, wherein the skin contact layer is coupled to the subassembly and is disposed on the skin-facing side of the at least one electrode element, wherein the skin contact layer is electrically coupled to the electrode and configured to contact skin of a subject, and wherein at least a portion of the skin contact layer is selectively removable from the subassembly.

Aspect 2: The apparatus of aspect 1, further comprising a first adhesive that couples the skin contact layer to the subassembly.

Aspect 3: The apparatus of any one of the preceding aspects, wherein the apparatus comprises a plurality of layers comprising conductive adhesive, wherein the plurality of layers comprise an outermost layer that forms the skin contact layer and at least one intermediate layer disposed between the at least one electrode element and the skin contact layer, wherein the skin contact layer is coupled to the at least one intermediate layer, and wherein the skin contact layer is configured to be decoupled from the at least one intermediate layer.

Aspect 4: The apparatus of aspect 3, wherein, upon decoupling the skin contact layer from the at least one intermediate layer, the at least one intermediate layer is configured to form an outermost skin contact layer.

Aspect 5: The apparatus of aspect 4, wherein the at least one intermediate layer comprises a plurality of intermediate layers that are configured to sequentially form the outermost skin contact layer upon separation of respective adjacent layers of conductive adhesive of the plurality of layers comprising conductive adhesive from the subassembly.

Aspect 6: The apparatus of any one of the preceding aspects, wherein the subassembly further comprises a layer of anisotropic material having a skin-facing side with a skin-facing surface and an opposing outwardly facing surface, wherein the at least one electrode element is in electrical contact with the outwardly facing surface of the layer of anisotropic material, and wherein the skin contact layer is disposed on the skin-facing side of the layer of anisotropic material.

Aspect 7: The apparatus of any one of the preceding aspects, wherein the skin contact layer comprises a conductive adhesive composite.

Aspect 8: A method comprising:
coupling, to a subassembly comprising at least one electrode element having a skin-facing side and a skin-facing surface, a skin contact layer comprising a conductive adhesive so that the skin contact layer is disposed on the skin-facing side of the at least one electrode element.

Aspect 9: The method of aspect 8, wherein the subassembly further comprises a pre-existing skin contact layer, wherein coupling the skin contact layer to the subassembly comprises coupling the skin contact layer to the pre-existing skin contact layer.

Aspect 10: The method of aspect 8, wherein the subassembly further comprises a pre-existing skin contact layer, the method further comprising, prior to coupling the skin contact layer to the subassembly, removing the pre-existing skin contact layer from the subassembly.

Aspect 11: The method of aspect 8, wherein the subassembly further comprises a first adhesive that couples the skin contact layer to the subassembly.

Aspect 12: The method of any one of aspects 8-11, wherein the subassembly further comprises a layer of anisotropic material having a skin-facing side with a skin-facing surface and an opposing outwardly facing surface, wherein the at least one electrode element is in electrical contact with the outwardly facing surface of the layer of anisotropic material, and wherein the coupling comprises coupling the skin contact layer to the subassembly so that the skin contact layer is disposed on the skin-facing side of the layer of anisotropic material.

Aspect 13: The method of aspect 12, wherein each of the layer of anisotropic material and the skin contact layer defines a respective circumferential edge, the method further comprising trimming the circumferential edge of the skin contact layer to align with the circumferential edge of the layer of anisotropic material.

Aspect 14: The method of any one of aspects 8-13, wherein the skin contact layer comprises a conductive adhesive composite.

Aspect 15: The method of any one of aspects 9-14, wherein the pre-existing skin contact layer comprises a conductive adhesive composite.

Aspect 16: A method comprising:
removing a skin contact layer from an assembly, the assembly comprising:
at least one electrode element having a skin-facing surface;
a plurality of layers of conductive adhesive comprising:
an outermost conductive adhesive layer that defines the skin contact layer; and
at least one intermediate layer disposed between the at least one electrode element and the skin contact layer,
wherein removing the skin contact layer from the assembly comprises removing the skin contact layer from the at least one intermediate layer, thereby exposing the at least one intermediate layer to define a new skin contact layer.

Aspect 17: The method of aspect 16, wherein the at least one intermediate layer comprises a plurality of intermediate layers that are configured to sequentially form the outermost skin contact layer upon separation of respective adjacent outermost layers of conductive adhesive of the plurality of layers of conductive adhesive from the assembly.

Aspect 18: The method of any one of aspects 16-17, wherein the assembly further comprises a layer of anisotropic material having a skin-facing side with a skin-facing surface and an opposing outwardly facing surface, wherein the at least one electrode element is in electrical contact with the outwardly facing surface of the layer of anisotropic material, and wherein the skin contact layer is disposed on the skin-facing side of the layer of anisotropic material.

Aspect 19: The method of any one of aspects 16-18, wherein the skin contact layer comprises a conductive adhesive composite.

Aspect 20: The method of any one of aspects 16-19, wherein, following the step of removing the skin contact layer from the assembly, the method further comprises adding a new skin contact layer comprising a conductive adhesive composite.

Aspect 21: The apparatus of any one of aspects 1-7, wherein the skin contact layer comprises a hydrogel.

Aspect 22: The method of aspect 16, wherein, upon removing the skin contact layer from the at least one intermediate layer, the at least one intermediate layer is configured to form an outermost skin contact layer.

Aspect 23: The method of any one of aspects 16-18, wherein each of the plurality of conductive adhesive layers comprises a conductive adhesive composite.

Aspect 24: The apparatus of aspect 7, wherein the conductive adhesive composite comprises a dielectric material and conductive particles dispersed within the dielectric material, wherein the conductive particles comprise carbon flakes, carbon granules, carbon fibers, carbon nanotubes, single-walled carbon nanotubes, multi-walled carbon nanotubes, carbon black powder, graphite powder, carbon nanowires, carbon microcoils, or any combination thereof.

Aspect 25: The method of aspect 14 or aspect 15, wherein the conductive adhesive composite comprises a dielectric material and conductive particles dispersed within the dielectric material, wherein the conductive particles comprise carbon flakes, carbon granules, carbon fibers, carbon nanotubes, single-walled carbon nanotubes, multi-walled carbon nanotubes, carbon black powder, graphite powder, carbon nanowires, carbon microcoils, or any combination thereof.

Aspect 26: The method of any one of aspects 19, 20, or 23 Wherein the conductive adhesive composite comprises a dielectric material and conductive particles dispersed within the dielectric material, wherein the conductive particles comprise carbon flakes, carbon granules, carbon fibers, carbon nanotubes, single-walled carbon nanotubes, multi-walled carbon nanotubes, carbon black powder, graphite powder, carbon nanowires, carbon microcoils, or any combination thereof.

Aspect 27: The method of any one of aspects 9-15, wherein the skin contact layer is part of a two layer unit or a three layer unit, wherein the two layer unit comprises a layer of anisotropic material and a skin contact layer; and the three layer unit comprises a layer of conductive material, a layer of anisotropic material, and a skin contact layer.

Aspect 27: The method of any one of aspects 18-20, wherein removing the skin contact layer from the assembly comprises removing a two layer unit or a three layer unit from the assembly, wherein the two layer unit comprises a layer of anisotropic material and a skin contact layer; and the three layer unit comprises a layer of conductive material, a layer of anisotropic material, and a skin contact layer.

Aspect 28: A kit comprising:
a plurality of replaceable units, each replaceable unit comprising a layer of anisotropic material and a skin contact layer coupled to the anisotropic layer.

Aspect 29: The kit of aspect 28, wherein the unit is a two-layer unit comprising the layer of anisotropic material and the skin contact layer.

Aspect 30: The kit of aspect 28, wherein the unit is a three-layer unit comprising the layer of anisotropic material, the skin contact layer, and a layer of conductive material, wherein the layer of anisotropic material is disposed between the skin contact layer and the layer of conductive material.

wherein the skin contact layer is part of a two layer unit or a three layer unit, wherein the two layer unit comprises a layer of anisotropic material and a skin contact layer; and the three layer unit comprises a layer of conductive material, a layer of anisotropic material, and a skin contact layer Aspect 31: A method comprising:
coupling, to a subassembly comprising at least one electrode element having a skin-facing side and a skin-facing surface, a skin contact layer comprising a conductive adhesive so that the skin contact layer is disposed on the skin-facing side of the at least one electrode element, wherein the skin contact layer has an in-plane conductivity and a conductivity perpendicular to the in-plane conductivity, wherein the in-plane conductivity is substantially equal to the conductivity perpendicular to the in-plane conductivity.

Aspect 32: A method comprising:
coupling, to a subassembly comprising at least one electrode element having a skin-facing side and a skin-facing surface, a skin contact layer comprising a conductive adhesive so that the skin contact layer is disposed on the skin-facing side of the at least one electrode element, wherein the skin contact layer has an in-plane conductivity and a conductivity perpendicular to the in-plane conductivity, wherein the in-plane conductivity is at least two times greater than the conductivity perpendicular to the in-plane conductivity.

While the present invention has been disclosed with reference to certain embodiments, numerous modifications, alterations, and changes to the described embodiments are possible without departing from the sphere and scope of the present invention, as defined in the appended claims. Accordingly, it is intended that the present invention not be limited to the described embodiments, but that it has the full scope defined by the language of the following claims, and equivalents thereof.

What is claimed is:

1. An apparatus comprising:
a subassembly comprising at least one electrode element having a skin-facing side and a skin-facing surface; and
a plurality of layers comprising conductive adhesive, wherein the plurality of layers comprise an outermost layer that forms a skin contact layer and at least one intermediate layer disposed between the at least one electrode element and the skin contact layer, wherein the skin contact layer is coupled to the at least one intermediate layer, and wherein the skin contact layer is configured to be decoupled from the at least one intermediate layer, wherein the skin contact layer is electrically coupled to the subassembly and is disposed on the skin-facing side of the at least one electrode element, wherein the skin contact layer is electrically coupled to the electrode and configured to contact skin of a subject, and wherein at least a portion of the skin contact layer is selectively removable from the at least one intermediate layer, wherein, upon decoupling the skin contact layer from the at least one intermediate layer, the at least one intermediate layer is configured to form an outermost skin contact layer.

2. The apparatus of claim 1, further comprising a first adhesive that couples the skin contact layer to the subassembly.

3. The apparatus of claim 1, wherein the subassembly further comprises a layer of anisotropic material having a skin-facing side with a skin-facing surface and an opposing outwardly facing surface, wherein the at least one electrode element is in electrical contact with the outwardly facing surface of the layer of anisotropic material, and wherein the skin contact layer is disposed on the skin-facing side of the layer of anisotropic material.

4. The apparatus of claim 1, wherein the skin contact layer is part of a two-layer unit or a three-layer unit, wherein the two-layer unit comprises a layer of anisotropic material and a skin contact layer; and the three-layer unit comprises a layer of conductive material, a layer of anisotropic material, and a skin contact layer.

5. The apparatus of claim 1, wherein the skin contact layer comprises a conductive adhesive composite.

6. The apparatus of claim 1, wherein the skin contact layer comprises a dielectric material and conductive particles dispersed within the dielectric material, wherein the conductive particles comprise carbon flakes, carbon granules, carbon fibers, carbon nanotubes, single-walled carbon nanotubes, multi-walled carbon nanotubes, carbon black powder, graphite powder, carbon nanowires, carbon microcoils, or any combination thereof.

7. A method comprising:

coupling, to a subassembly comprising at least one electrode element having a skin-facing side and a skin-facing surface and a pre-existing skin contact layer, a skin contact layer comprising a conductive adhesive so that the skin contact layer is disposed on the skin-facing side of the at least one electrode element, wherein coupling the skin contact layer to the subassembly comprises coupling the skin contact layer to the pre-existing skin contact layer.

8. The method of claim 7, wherein the subassembly further comprises a first adhesive that couples the skin contact layer to the subassembly.

9. The method of claim 7, wherein the subassembly further comprises a layer of anisotropic material having a skin-facing side with a skin-facing surface and an opposing outwardly facing surface, wherein the at least one electrode element is in electrical contact with the outwardly facing surface of the layer of anisotropic material, and wherein the coupling comprises coupling the skin contact layer to the subassembly so that the skin contact layer is disposed on the skin-facing side of the layer of anisotropic material.

10. The method of claim 7, wherein the skin contact layer comprises a conductive adhesive composite.

11. The method of claim 7, wherein the pre-existing skin contact layer comprises a conductive adhesive composite.

12. The method of claim 7, wherein the skin contact layer is part of a two-layer unit or a three-layer unit, wherein the two-layer unit comprises a layer of anisotropic material and a skin contact layer; and the three-layer unit comprises a layer of conductive material, a layer of anisotropic material, and a skin contact layer.

13. The method of claim 7, wherein the skin contact layer comprises a dielectric material and conductive particles dispersed within the dielectric material, wherein the conductive particles comprise carbon flakes, carbon granules, carbon fibers, carbon nanotubes, single-walled carbon nanotubes, multi-walled carbon nanotubes, carbon black powder, graphite powder, carbon nanowires, carbon microcoils, or any combination thereof.

14. A method comprising:

removing a skin contact layer from an assembly, the assembly comprising:

at least one electrode element having a skin-facing surface; and a plurality of layers of conductive adhesive comprising:

an outermost conductive adhesive layer that defines the skin contact layer; and at least one intermediate layer disposed between the at least one electrode element and the skin contact layer, wherein removing the skin contact layer from the assembly comprises removing the skin contact layer from the at least one intermediate layer, thereby exposing the at least one intermediate layer to define a new skin contact layer.

15. The method of claim 14, wherein the at least one intermediate layer comprises a plurality of intermediate layers that are configured to sequentially form the outermost skin contact layer upon separation of respective adjacent outermost layers of conductive adhesive of the plurality of layers of conductive adhesive from the assembly.

16. The method of claim 14, wherein the assembly further comprises a layer of anisotropic material having a skin-facing side with a skin-facing surface and an opposing outwardly facing surface, wherein the at least one electrode element is in electrical contact with the outwardly facing surface of the layer of anisotropic material, and wherein the skin contact layer is disposed on the skin-facing side of the layer of anisotropic material.

17. The method of claim 16, wherein removing the skin contact layer from the assembly comprises removing a two-layer unit or a three-layer unit from the assembly, wherein the two-layer unit comprises a layer of anisotropic material and a skin contact layer; and the three-layer unit comprises a layer of conductive material, a layer of anisotropic material, and a skin contact layer.

18. The method of claim 14, wherein the skin contact layer comprises a conductive adhesive composite.

19. The method of claim 14, wherein, following the step of removing the skin contact layer from the assembly, the method further comprises adding a new skin contact layer comprising a conductive adhesive composite.

20. The method of claim 14, wherein the skin contact layer comprises a dielectric material and conductive particles dispersed within the dielectric material, wherein the conductive particles comprise carbon flakes, carbon granules, carbon fibers, carbon nanotubes, single-walled carbon nanotubes, multi-walled carbon nanotubes, carbon black powder, graphite powder, carbon nanowires, carbon microcoils, or any combination thereof.

* * * * *